US010921330B2

(12) United States Patent
Bergmann et al.

(10) Patent No.: US 10,921,330 B2
(45) Date of Patent: Feb. 16, 2021

(54) METHOD FOR DIAGNOSIS OF DEMENTIAS AND NEUROINFLAMMATORY DISEASES BASED ON AN INCREASED LEVEL OF PROCALCITONIN IN CEREBROSPINAL FLUID

(71) Applicant: B.R.A.H.M.S GmbH, Hennigsdorf (DE)

(72) Inventors: Andreas Bergmann, Berlin (DE); Andrea Sparwaβer, Hennigsdorf (DE); Harald Hampel, Munich (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 25 days.

(21) Appl. No.: 14/966,843

(22) Filed: Dec. 11, 2015

(65) Prior Publication Data
US 2016/0097782 A1 Apr. 7, 2016

Related U.S. Application Data

(63) Continuation of application No. 11/996,213, filed as application No. PCT/EP2006/007141 on Jul. 19, 2006, now abandoned.

(30) Foreign Application Priority Data

Jul. 21, 2005 (DE) .................... 10 2005 034 174.8

(51) Int. Cl.
| | | |
|---|---|---|
| *A61K 49/00* | (2006.01) | |
| *A61K 49/16* | (2006.01) | |
| *A61B 5/00* | (2006.01) | |
| *G01N 33/53* | (2006.01) | |
| *G01N 33/74* | (2006.01) | |
| *G01N 33/68* | (2006.01) | |
| *G01N 33/50* | (2006.01) | |
| *G01N 33/557* | (2006.01) | |
| *A61K 38/16* | (2006.01) | |
| *C07K 16/18* | (2006.01) | |
| *A61K 38/23* | (2006.01) | |
| *G01N 33/48* | (2006.01) | |

(52) U.S. Cl.
CPC ............ *G01N 33/74* (2013.01); *G01N 33/50* (2013.01); *G01N 33/53* (2013.01); *G01N 33/6896* (2013.01); *A61K 38/16* (2013.01); *A61K 38/23* (2013.01); *C07K 16/18* (2013.01); *G01N 33/48* (2013.01); *G01N 33/557* (2013.01); *G01N 2333/00* (2013.01); *G01N 2333/435* (2013.01); *G01N 2333/585* (2013.01); *G01N 2800/28* (2013.01); *G01N 2800/2814* (2013.01); *G01N 2800/2821* (2013.01); *G01N 2800/56* (2013.01)

(58) Field of Classification Search
CPC ......... G01N 2333/585; G01N 33/6896; G01N 33/74; G01N 2333/475; G01N 2333/52; G01N 2800/2821; G01N 2800/52; G01N 2800/2814; G01N 2333/575; G01N 2333/598; G01N 2800/2835; C07K 14/575; C07K 16/2896; C07K 2317/55; C07K 14/47; C07K 14/4711; C07K 16/18; C07K 16/26; C07K 2317/21; C07K 2317/565; C07K 2318/10; A61K 31/00; A61K 2039/505; A61K 2300/00; A61K 38/07; A61K 45/06

See application file for complete search history.

(56) References Cited

U.S. PATENT DOCUMENTS

| | | | | |
|---|---|---|---|---|
| 2002/0052471 | A1* | 5/2002 | Althaus ................ | C07K 14/585 530/350 |
| 2004/0121343 | A1* | 6/2004 | Buechler ............. | C12Q 1/6883 435/6.14 |
| 2004/0209307 | A1* | 10/2004 | Valkirs ................ | C12Q 1/6883 435/7.1 |
| 2004/0219509 | A1* | 11/2004 | Valkirs ................ | C12Q 1/6883 435/4 |
| 2004/0253637 | A1* | 12/2004 | Buechler ............ | A61B 5/14546 435/7.1 |
| 2005/0148029 | A1* | 7/2005 | Buechler ............. | C12Q 1/6883 435/7.1 |
| 2005/0164238 | A1* | 7/2005 | Valkirs ............... | G01N 33/6893 435/6.16 |
| 2005/0255484 | A1* | 11/2005 | Valkirs ............... | G01N 33/6896 435/6.16 |
| 2008/0206797 | A1 | 8/2008 | Bergmann et al. | |

OTHER PUBLICATIONS

Morgenthaler et al., Clinical Chemistry 2002; 48:788-789.*
Jereb M. et al., "Predictive value of serum and cerebrospinal fluid procalcitonin levels for the diagnosis of bacterial meningitis", Infection, vol. 29(4), Aug. 2001, 209-212.
Morgenthaler N. G. et al., "Sensitive immunoluminometric assay for the detection of procalcitonin", Clinical Chemistry 2002 United States. vol. 48(5), 788-790.
Morgenthaler Nils G. et al., "Detection of procalcitonin (PCT) in healthy controls and patients with local infection by a sensitive ILMA", Clinical Laboratory, 2002, vol. 48(5-6), 263-270.
Steinbach Gerald et al., "Multicenter evaluation of new immunoassay for procalcitonin measurement on the Kryptor (R) system", Clinical Chemistry and Laboratory Medicine, vol. 42(4), 2004, 440-449.

(Continued)

*Primary Examiner* — Chang-Yu Wang
(74) *Attorney, Agent, or Firm* — Troutman Pepper Hamilton Sanders LLP

(57) ABSTRACT

CSF diagnostic in vitro method for the diagnosis of dementias and neuroinflammatory diseases, in which a determination of the procalcitonin immunoreactivity (PCT immunoreactivity) is carried out in a sample of cerebrospinal fluid (CSF) of a patient who is suffering from a dementia or neuroinflammatory disease or is suspected of suffering from such a disease. Conclusions about the presence, the course, the severity or the success of a treatment of the dementia or neuroinflammatory disease are drawn from a measured PCT immunoreactivity which is above a threshold value typical for healthy individuals.

5 Claims, 1 Drawing Sheet

(56) References Cited

OTHER PUBLICATIONS

Van Rossum A. et al., "Procalcitonin as an early marker of infection in neonates and children" Lancet Infectious Diseases, US, vol. 4(10), Oct. 2004, 620-630.
International Preliminary Report on Patentability and Written Opinion of the ISA for corresponding PCT patent application No. PCT/EP2006/007141.
Bergmann et al., Abstract "Procalcitonin in Cerebrospinal Fluid is Elevated in Patients with Dementia and Acute Neuroinflammation", "P2-149" Alzheimer's & Dementia: The Journal of Alzheimer's Association, Elsevier, New York, NY, US, vol. 2(3), Jul. 5, 2006, p. S277.
Akiyama H. and The Neuroinflammation Working Group (2000), Inflammation and Alzheimer's Disease. Neurobiology of Aging 21: 383-421.
Assicot M., et al., (1993), "High serum procalcitonin concentrations in patients with sepsis and infection", The Lancet vol. 341(8844), 515-518.
Becker K. L., et al., "Procalcitonin and the Calcitonin Gene Family of Peptides in Inflammation, Infection, and Sepsis: a Journey from Calcitonin back to its Precursors". Journal of Clinical Endocrinology and Metabolism, Apr. 2004. vol. 89(4), 1512-1525.
Caplan Louis, et al., "Clinical Features of Subcortical Arteriosclerotic Encephalopathy (Binswanger's disease)", Dec. 1978, Neurology 28: 1206-1215.
Dandona P., et al., "Procalcitonin Increase after Endotoxin Injection in Normal Subjects", Journal of Clinical Endocrinology and Metabolism, 1994, vol. 79(5), 1605-1608.
Geldmacher David S., M.D., "Dementia with Lewy bodies: Diagnosis and clinical approach", Cleveland Clinic Journal of Medicine, vol. 71(10), Oct. 2004, 789-800.
Gendrel D., et al., "Procalcitonin as a marker for the early diagnosis of neonatal infection". The Journal of Pediatrics, vol. 128(4): 570-573.
Gendrel D., et al., "Measurment of Procalcitonin levels in Children with Bacterial or Viral Meningitis", Clinical Infectious Diseases, Jun. 1997, 24:1240-1242.
Hachinski V.C., et al., "Multi-infarct Dementia: a cause of Mental Deterioration in Elderly", The Lancet, Jul. 27, 1984, 207-209.
Han Y., et al., "Cerebrospinal fluid Procalcitonin and Severe Traumatic Brain Injury in Children". Pediatric Critical Care Medicine 2002, vol. 3(1), 39-44.
Holmes C., et al., "Validity of Current Clinical Criteria for Alzheimer's Disease, Vascular Dementia and Dementia with Lewy bodies", British Journal of Psychiatry (1999) 174: 45-50.
Katsuse O., "Immunohistochemical Study of the Expression of Cytokines and Nitric Oxide Synthases in Brains of Patients with Dementia with Lewy Bodies", Neuropathology 2003, 23: 9-15.
MacKenzie I.R., "Activated Microglia in Dementia with Lewy Bodies", Neurolology 55: 132-134.
MacKenzie I.R., "Cortical Inflammation in Dementia with Lewy Bodies", Arch Neurology, vol. 58, Mar. 2001, 519-520.
McKeith I.G., et al., "Consensus Guidelines for the Clinical and Pathologic Diagnosis of Dementia with Lewy Bodies (DLB): Report of the Consortium on DLB International Workshop", Nov. 1996, Neurology 47: 1113-1124.
McKeith I.G., et al., "Diangosing Dementia with Lewy Bodies", Oct. 9, 1999, The Lancet. vol. 354: 1227-1228.
McKeith I.G., et al., "Dementia with Lewy Bodies", British Journal of Psychiatry 180: 144-147.
Mueller B., et al., "Calcitonin Precursors are Reliable Markers of Sepsis in a Medical Intensive Care Unit", Critical Care Medicine 2000, vol. 28(4), 977-983.
O'Connor E., et al., "Procalcitonin in Critical Illness". Critical Care and Resuscitation 2001; vol. 3: 236-243.
Rizzu P., et al., "High Prevalence of Mutations in the Microtubule-Associated Protein Tau in a Population Study of Frontotemporal Dementia in the Netherlands", American Journal of Genetics, 1999, vol. 64, 414-421.
Selkoe D.J., Alzheimer's Disease: Genes, Proteins, and Therapy, Physiological Reviews, Apr. 2001, vol. 81(2): 741-766.
Shimetani N., et al., "Level of Three Inflammation Markers. C-Reactive Protein, Serum Amyloid A Protein and Procalcitonin, in the Serum and Cerebrospinal Fluid of Patients with Meningitis", Scandinavian Journal of Clinical and Laboratory Investigation, 2001, vol. 61, 567-574.
Sjogren M., et al., "Increased Intrathecal Inflammatory Activity in Frontotemporal Dementia: Pathophysiological Implications", Journal of Neurology and Neurosugical Psychiatry, 2004; vol. 75: 1107-1111.
Snider R.H. Jr., et al., "Procalcitonin and its Component Peptides in Systemic Inflammation, Immunochemical Characterization", Journal of Investigative Medicine, Dec. 1997, vol. 45(9): 552-560.
Spencer C.A., et al., Applications of a new Chemiluminometric Thyrotropin Assay to Subnormal Measurement. Journal of Clinical Endocrinology Metab.,1990, vol. 70(2): 453-460. Abstract Only.
Tarkowski E., "Cytokines in Dementias". Current Drug Targets—Inflammation & Allergy, 2002, vol. 1(2), 193-200.
Tarkowski E., et al., "Cerebral Pattern of Pro- and Anti-inflammatory Cytokines in Dementias", Brain Research Bulletin 61 (2003): 255-260.
Teunissen C.E., et al., "Biochemical Makers Related to Alzheimer's Dementia in Serum and Cerebrospinal Fluid", (2002) Neurobiology of Aging 23, 485-508.
Varma A.R., et al., "Evaluation of the NINCDS-ADRDA Criteria in the Differentiation of Alzheimer's Disease and Frontotemporal Dementia", Journal of Neurology, Neurosurgery and Psychiatry (1999) vol. 66: 184-188.
Whang K.T., et al., "Serum Calcitonin Precursors in Sepsis and Systemic Inflammation", Journal of Clinical Endocrinology and Metabolism, (1998), vol. 83(9), 3296-3301.
Whicher I., et al., Procalcitonin as an Acute Phase Marker, Annals of Clinical Biochemistry 2001. vol. 38: 483-493.
Zhukareva V. et al., "Loss of Brain Tau Defines Novel Sporadic and Familial Tauopathies with Frontotemporal Dementia", Annals of Neurology, Feb. 2001. vol. 49(2): 165-175.

* cited by examiner

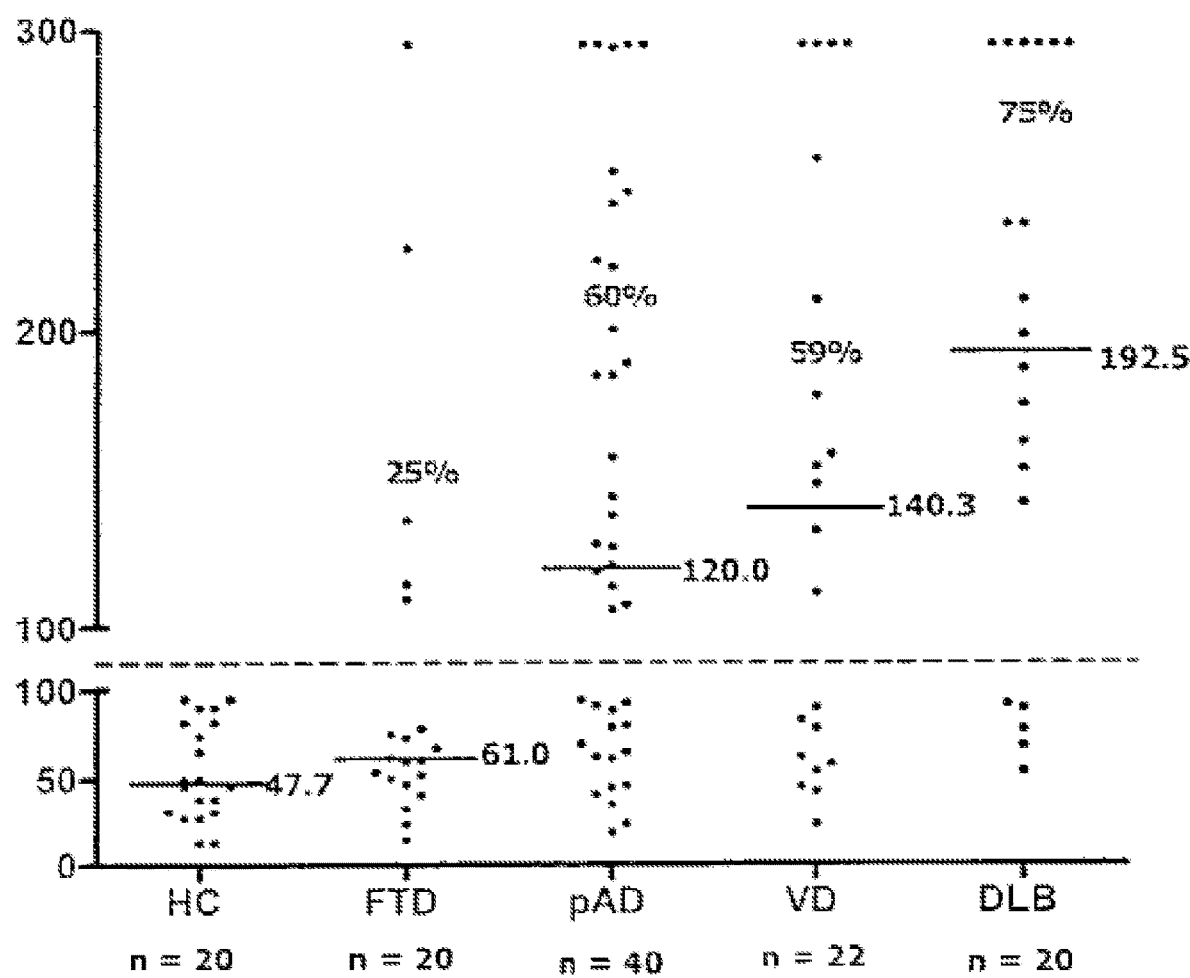

METHOD FOR DIAGNOSIS OF DEMENTIAS AND NEUROINFLAMMATORY DISEASES BASED ON AN INCREASED LEVEL OF PROCALCITONIN IN CEREBROSPINAL FLUID

CROSS REFERENCE TO RELATED APPLICATIONS

This application is a continuation of copending U.S. application Ser. No. 11/996,213 filed Jan. 18, 2008, now abandoned, which is a national stage of PCT International Application No. PCT/EP2006/007141, filed on Jul. 19, 2006, and published in German on Jan. 25, 2007, as WO 2007/009789 A1, which claims priority to German Application No. 10 2005 034 174.8 filed on Jul. 21, 2005. The entire disclosures of these applications are incorporated herein by reference in their entirety.

The present invention relates to a novel CSF diagnostic in vitro method for diagnosis of dementias and neuroinflammatory diseases.

In the context of the present invention, the term "diagnosis" is used as a general term for medical determinations which, depending on the clinical state of the patient for whom the determination is carried out, may be based on different problems and which serve in particular for detection and early detection, determination of severity and monitoring, including monitoring during the treatment, and prognosis of the future course of the disease.

The method according to the invention is a CSF diagnostic in vitro method. A CSF diagnostic method is understood as meaning a method which is usually carried out in the course of the diagnosis of neurological diseases and in which the determination of a property of the so-called cerebrospinal fluid (CSF) which is informative for diagnostic purposes is effected. In the case of the present invention, the specific property is the immunodiagnostically determinable content of a biomolecule in the CSF.

The diseases which are diagnosed according to the present invention are in particular presenile dementias, as will be discussed in more detail in the present Application, and further chronic neuroinflammatory diseases of non-infectious aetiology.

Dementias are generally defined as diseases for which a common feature is the loss of acquired intellectual capabilities, especially of the memory, and of the normal level of the personality as a consequence of brain damage. Dementias are as a rule relatively slowly developing diseases of chronic character. If dementia phenomena occur before old age, in middle aged people, they are referred to as presenile dementias and, on the basis of the symptoms typical of them and pathological changes in the brain, a differentiation is made in particular between the following four diseases or groups of diseases:

Alzheimer's dementia (AD) (Alzheimer's disease) is the most frequent neurodegenerative dementia and accounts for ⅔ of all cases of dementia. AD is distinguished by three important pathological features: the formation of amyloid plaques and neurofibrillar bundles and the loss of nerve cells (for an overview, cf. 24; references in the description in the form of numbers refer to the list of references following the description). Amyloid plaques consist of extraneuronal aggregates of amyloid-β-protein, while the neurofibril bundles contain mainly tau-protein and neurofilaments. It is presumed that the plaque and neurofibril formation is the cause of the death of nerve cells.

The most important symptoms of AD are increasing dysfunctions of memory and intellect with relatively persistent emotional responsiveness, these symptoms being accompanied by further less specific disturbances which make it difficult to differentiate AD from other forms of dementia.

Dementia with Lewy bodies (DLB) is the second most frequent cause of a dementia after Alzheimer's dementia (11; 18). Neuropathologically, DLB is characterized by the occurrence of so-called Lewy bodies in the brain stem and in the cortex. These Lewy bodies consist predominantly of aggregates of the presynaptic protein (α-synuclein) and ubiquitin. Lewy body pathology can be associated to different extents with neuropathological changes typical of Alzheimer's and Parkinson's disease. Thus, in DLB too, the formation of β-amyloid and senile plaques occurs, but not neurofibril bundles (for an overview, cf. 6). Lewy bodies are also present in the brain of patients with Parkinson's disease, even if in a different distribution (for an overview cf. 19).

Key symptoms of DLB are a progressive cognitive disturbance, episodes of confusion with fluctuating attention and consciousness, Parkinsonism, frequent falls and syncopes (brief, paroxysmal unconsciousness) (17). The sensitivity and specificity of the diagnostic criteria (17) show high specificity throughout but a very low sensitivity in some cases. This means that DLB is frequently not diagnosed in clinical routine. In particular the differentiation from Alzheimer's disease must be further improved.

Frontotemporal dementia (FTD) is also referred to as Pick's disease and accounts for about 20% of presenile dementias. FTD is genetic in some cases and is among the so-called tauopthies, which are distinguished by overexpression or underexpression of a tau-protein subtype (34) or by the expression of a mutated tau-protein (23). Neuropathological symptoms are local atrophy of the frontal and/or temporal cortex and of the substantia nigra and of the basal ganglia. This results in different levels of speech disturbance, a change of personality and behavioural peculiarities. Overall, FTD is underdiagnosed with a sensitivity of 93% and a specificity of only 23%, AD being the most frequent misdiagnosis (30).

The term vascular dementia (VAD) covers diseases in which a dementia is triggered owing to disturbed blood flow in the brain. There are different types of VAD, of which multi-infarction dementia (MID) and subcortical VAD (also referred to as Binswanger's disease) are the most frequent forms.

Binswanger's disease is a slowly progressing dementia which is characterized pathologically by cerebrovascular lesions in the white brain substance. Clinically this results in behavioural peculiarities, such as agitation, irritability, depression and euphoria, and slight memory disturbance (4).

Multi-infarction dementia arises gradually as a consequence of several small strokes, also referred to as transient ischaemic attacks (TIA), which led to the destruction of brain tissue in the cortex and/or subcortical areas (9). The strokes may also have remained completely unnoticed, in which case the dementia is the first noticeable consequence. In the presence of MID, there is a gradual decrease in cognitive capabilities, associated with severe depressions, mood fluctuations and epilepsy.

A diagnosis of dementias is performed nowadays predominantly on the basis of neuropsychological investigations and the observation of the development of the disease and its course using exclusion criteria for certain forms of dementia. In very many cases, these investigations give ambiguous results, which explain the abovementioned numbers for the underdiagnosed forms of dementia or incorrectly diagnosed cases. The cerebral changes typical of the disease cannot of course be established directly in living patients and technical medical investigations of brain function by means of, for example, X-ray tomography or MRI are complicated and expensive.

There is a need for supplementary methods of investigation which permit diagnosis of dementia and which facilitate in particular the differentiation of different forms of dementia with similar or blurred clinical symptoms, an immunodiagnostic determination of biomarkers of a suitable specificity and sensitivity being particularly desirable.

The present invention provides such a method of investigation in the form of a CSF diagnostic in vitro method for detection and early detection, for the determination of severity and for monitoring and prognosis of dementias and neuroinflammatory diseases according to claim 1, in which a determination of the procalcitonin immunoreactivity (PCT immunoreactivity) is carried out in a sample of the cerebrospinal fluid (CSF) of a patient who is suffering from a dementia or neuroinflammatory disease or is suspected of suffering from such a disease, and conclusions about the presence, the type, the course, the severity or the success of a treatment of the dementia or neuroinflammatory disease are drawn from a measured PCT immunoreactivity, which is above a threshold value typical for healthy control persons.

In particular, the PCT determination in the CSF is effected, as emphasised in claim 2, with the aid of a highly sensitive PCT immunoassay having a functional assay sensitivity (FAS) of better than 100 ng of PCT per 1 (100 ng/l or 100 pg/ml), in particular better than 50 ng/l and particularly preferably better than 10 ng/l.

Advantageous developments of the method according to claims 1 and 2 are described in subclaims 3 to 12.

Since the measurements described in more detail below have shown that the PCT immunoreactivity in CSF can be measured with high precision and reliability by a highly sensitive immunoassay having a functional assay sensitivity (FAS) which is considerably better than that of the commercial PCT immunoassays available for sepsis diagnosis, while—as will be explained below—the isolated attempts to date with regard to a PCT determination in CSF by the known assays led to contradictory results providing little information, the invention also relates, according to claim 13, very generally to the use of a highly sensitive immunoassay for procalcitonin determination having a functional assay sensitivity (FAS) of 50 ng/l or better, in particular of 10 ng/l or better, for the determination of procalcitonin immunoreactivity in cerebrospinal fluid (CSF).

Functional assay sensitivity (FAS; also functional inter assay sensitivity) is defined as a parameter which indicates the analyte concentration which is measured by the respective method with an interassay precision (an interassay coefficient of variation) of ≤20% (35).

The present invention is based on considerations by the inventors for improving the diagnosis of dementias and in particular the differential diagnosis for distinguishing between different forms of presenile dementia by applying the discovery that the known forms of presenile dementia explained in more detail at the outset are also accompanied—to different extents—by inflammatory processes which are regarded as essential for the development, the symptoms and the course of dementias.

Thus, Alzheimer's disease is characterized, inter alia, by the occurrence of chronic local inflammatory reactions in the brain with participation of various inflammatory proteins, such as complement factors, acute-phase proteins and proinflammatory cytokines (1, 30).

Inflammatory processes also play a role in the origin of vascular dementias (VAD). The levels of TNFα, TGFβ, IL-6 and GM-CSF (granulocyte-macrophage colony-stimulating factor) are substantially elevated in patients with VAD (28; 29).

It is presumed that both in the case of AD and in the case of VAD a similar cytokine production cascade is started as a response to neuronal damage, although the triggering factors of these two forms of neurodegeneration are different and lead to different neuropathological changes in the brain (28).

In DLB, too, inflammatory processes appear to play a role. Thus, the number of activated microglia cells in the brain of patients with DLB is increased (15), and proinflammatory cytokines, such as TNFα, are overexpressed in certain regions of the brain, such as the amygdala and the hippocampus (13).

There are only sparse indications for the occurrence of inflammatory reactions in the brain of FTD patients. In a study by Sjogren et al., it was possible to measure significantly elevated concentrations of the pro-inflammatory cytokine TNFα and of the anti-inflammatory cytokine TGFβ in the cerebrospinal fluid of some FTD patients (26).

Against a background of extensive clinical material and extensive experience on the part of the Applicant which relates to the occurrence of the peptide procalcitonin (PCT) in the serum and plasma of sepsis patients and other patients, the inventors thought it a worthwhile problem to determine whether changes of PCT concentrations which can be related in a diagnostically relevant manner to dementias and other neuroinflammatory diseases can be determined in the CSF.

Procalcitonin (PCT) is a peptide which consists of 116 amino acids and was first discussed as a precursor of the important hormone calcitonin (thyreocalcitonin) and the complete amino acid sequence of which has been known just as long as the details of its proteolytic degradation which leads to the liberation of the mature hormone calcitonin and other shorter peptides, including in particular so-called katacalcin (procalcitonin 96-116) and an n-terminal peptide (n-procalcitonin 1-57), which are abbreviated herein to "PCT partial peptides". As explained in more detail, for example, in the patents EP 0 656 121 B1 and U.S. Pat. No. 5,639,617 and in (2), severe bacterial inflammations with systemic reaction result in the release of PCT into the circulation where it is found in very high, readily measurable amounts (2; cf. also the overviews in 22; 33; 3). Reference is made expressly to the general technical knowledge recorded in said patents and references for supplementing the present description. Viral, autoimmune and allergic diseases on the other hand do not lead to a significant increase in the PCT concentration in the blood. PCT reflects the severity of a bacterial infection and is used as a marker for the diagnosis and therapeutic monitoring of sepsis, severe sepsis and septic shock (5; 7; 27; 32; 21).

The determination of PCT may also be used for differential diagnostic purposes since inflammatory diseases of infectious aetiology can be distinguished from those of non-infectious aetiology on the basis of the measurable PCT concentrations in serum and plasma (cf. also EP 0 880 702 B1).

PCT is determined, as described in the abovementioned patents and references, in a suitable manner by immunoassays of the sandwich type using two antibodies which bind to the amino acid sequence of the complete PCT peptide so that the PCT processed completely with release of calcitonin is not detected but the total unprocessed PCT and optionally also those longer PCT partial peptides which have both binding sites for the antibodies used in the assay are detected. Since the sandwich assays used do not as such detect exclusively the complete unprocessed PCT, it is preferred in the present application to refer to the determination of a PCT immunoreactivity instead of a PCT determination, with the result that the appearance of a stipulation for an exclusive measurement of a molecule with the complete PCT sequence is to be avoided. In general, the measurement of the PCT immunoreactivity can be designated as a measurement by a sandwich immunoassay using two antibodies which bind to those segments of the complete PCT peptide which, in the proteolytic processing of PCT with formation of calcitonin, are located on different members of the PCT partial peptides formed or which are located on PCT partial peptides which do not comprise the calcitonin sequence.

The fact that it is not the complete PCT 1-116 which is determined in serum or plasma in the case of sepsis but a PCT 3-116 shortened by two amino acids is explained in EP 1 121 600 A1 and EP 1 48 334 A1 or U.S. Pat. No. 6,756,483, which are referred to for supplementing the present description.

For the determination of the procalcitonin immunoreactivities in serum/plasma, there exists, for example, the commercial chemiluminescence assay LUMItest® PCT (B.R.A.H.M.S. AG), which has a functional assay sensitivity (FAS) of 300 ng/l and is tailored to PCT determination in sepsis, where very high PCT concentrations can occur. For PCT determination with a higher sensitivity, a modified sandwich immunoassay which operates with an affinity-purified polyclonal antibody and which is described in more detail in (20) and is obtainable as LUMItest® PCTsensitiv (B.R.A.H.M.S AG) was recently developed. This assay has a clearly better FAS of 7 ng/l (20). With the aid of this assay, it was possible to determine a mean PCT serum concentration of 13.5 ng/l (13.5 pg/ml) in healthy persons, values from <7 to 63 ng/l having been found and the 97.5% percentile being 42.5 ng/l.

Data on experiments to measure PCT in CSF too, appear only sparsely in the scientific literature, and all measurements described were carried out under premises which cannot be logically related to the determination, according to the invention, of PCT in CSF for the diagnosis of dementias and further neuroinflammatory diseases:

Starting from the suitability of PCT as an infection marker, an attempt was made to determine whether PCT concentrations in the CSF of patients with meningitis (8; 12; 25) or Lyme borreliosis (14) are measurable and may permit a distinction between bacterial meningitis and viral meningitis. The findings were contradictory, either no increased measured values at all being obtained (8; 25) or only a weak indication being possible (12).

Starting from a genetic relationship between PCT and the peptide CGRP (calcitonin gene related peptide) and homologous sequence designations for adrenomedullin (ADM), which was measured at elevated levels in the CSF of children with traumatic brain injury (TBI), it was furthermore investigated whether elevated PCT concentrations can be found in the CSF in the case of such children too (10). There, it was possible to find elevated PCT concentrations, which were related to an acute-phase reaction to the trauma, even if the significance of the observations as a whole remained unclear. It is not possible to find any recognizable logical relationship with measurements in the case of dementias and further neuroinflammatory diseases which form the subject of the present invention.

In all cases where an attempt was made to determine PCT in the CSF, the commercial assay developed for sepsis diagnosis in serum or plasma, which had an FAS of only 300 ng/l, was employed.

The Applicants have reason to assume that considerably improved measured results with better diagnostic significance are obtained in the CSF also in the case of, for example, infectious diseases, such as bacterial meningitis, if measurements as described, for example, in (8; 12) are carried out by a highly sensitive PCT assay according to (20), as was used in the case of the measurements which form the basis of the present invention and are described in the experimental section. It should be pointed out that clear standard concentrations for healthy persons could be determined by such a highly sensitive assay under the conditions described. The present application therefore furthermore relates very generally to the measurement of PCT in the CSF by a highly sensitive immunoassay for diagnostic purposes.

Below, the invention is explained in more detail with reference to measured results and a FIGURE.

FIG. 1 shows the results of the measurement of the PCT immunoreactivity in the CSF of healthy normal persons (HC) and in the CSF of patients with four different diagnosed types of presenile dementias, namely frontotemporal dementia (FTD), Alzheimer's dementia (pAD), vascular dementia (VAD) and dementia with Lewy bodies (DLB), and with the median concentrations and sensitivities for the individual forms of dementia for the measured groups of patients.

EXPERIMENTAL SECTION

Description of Assay

The measurement of procalcitonin in the cerebrospinal fluid was effected as described in (20). However, the lyophilised standards were dissolved not in zero serum but in PBS (with 1% BSA).
Measurement of the PCT Immunoreactivity in the Cerebrospinal Fluid of Healthy Controls and Patients With Presenile Dementias Procalcitonin was detected with the LUMItest® PCTsensitiv (cf. 20) in cerebrospinal fluid of healthy control persons. It was possible to show that the concentrations are in the range between 12 and 133 ng/l (median concentration 50 ng/l). Since the median PCT concentration in the serum of healthy persons was determined only as 13.5 ng/l (20), there is a PCT concentration gradient between blood and CSF of about 1:4 in healthy persons.

The measured PCT concentrations in the cerebrospinal fluid of healthy controls and patients with different forms of presenile dementia are shown in FIG. 1.

The respective sensitivity and specificity of the highly sensitive LUMItest® PCTsensitiv assay for the diagnosis of different presenile dementias are shown in table 1.

TABLE 1

Specificity and sensitivity of the measurements of the PCT immunoreactivity in the CSF of patients with different dementias

| Dementia | Specificity (%) | Sensitivity (%) |
| --- | --- | --- |
| Subjective cognitive disturbances | 100 | 50 |

TABLE 1-continued

Specificity and sensitivity of the measurements of the PCT immunoreactivity in the CSF of patients with different dementias

| Dementia | Specificity (%) | Sensitivity (%) |
|---|---|---|
| Frontotemporal dementia | 100 | 25 |
| Alzheimer's dementia* | 100 | 60 |
| Vascular dementia | 100 | 59 |
| Dementia with Lewy bodies | 100 | 75 |

Group of patients diagnosed with "probable Alzheimer's disease" (pAD), the diagnosing institution having a mean statistical reliability for Alzheimer diagnosis of 90%.

According to FIG. 1, the measured results show different median concentrations for the different patient groups, the group of FTD patients (patients with subjective cognitive disturbances) giving on average only slightly higher measured values than healthy persons and differing substantially from the other patient groups in whom the mean PCT concentrations (i) were considerably elevated compared with healthy persons, and (ii) also differed from group to group. DLB patients had the highest measurable PCT concentrations and were found to be positive with a high sensitivity of 75% (within the clinically presorted groups; specificity 100%).

LITERATURE

1. AKIYAMA H. AND THE NEUROINFLAMMATION WORKING GROUP (2000). Inflammation and Alzheimer. Neurobiology of Aging 21: 383-421
2. ASSICOT M., GENDREL D., CARSIN H., RAYMOND J., GUILBAUD J., BOHUON C. (1993). High serum Procalcitonin concentrations in patients with sepsis and infection. Lancet 341: 515-518
3. BECKER K. L., NYLEN E. S., WHITE J. C., MUELLER B., SNIDER R. H. (2004). Procalcitonin and the calcitonin gene family of peptides in inflammation, infection, and sepsis: a journey from calcitonin back to its precursors. Journal of Clinical Endocrinology and Metabolism 89: 1512-1525
4. CAPLAN L., SCHOENE W. C. (1978). Clinical features of subcortical arteriosclerotic encephalopathy (Binswanger's disease). Neurology 28: 1206-1215
5. DANDONA P., NIX D., WILSON M. F., ALJADA A., LOVE J., ASSICOT M., BOHUON C. (1994). Procalcitonin increase after endotoxin injection in normal subjects. Journal of Clinical Endocrinolgy and Metabolism 79: 1605-1608
6. GELDMACHER D. S. (2004). Dementia with lewy bodies: diagnosis and clinical approach. Cleveland clinic Journal of Medicine 71: 789-800
7. GENDREL D., ASSICOT M., RAYMOND J., MOULIN F., FRANCOUAL C., BADOUAL J., BOHOUN C. (1996). Procalcitonin as a marker for the early diagnosis of neonatal infection. Journal of Pediatrics 128: 570-573
8. GENDREL D., RAYMOND J., ASSICOT M., MOULIN F., INIGUEZ J.-L., LEBON P., BOHUON C. (1997). Measurement of Procalcitonin levels in children with bacterial or viral meningitis. Clinical Infectious Diseases 24: 1240-1242
9. HACHINSKI V. C., LASSEN N. A., MARSHALL J. (1974). Multi-infarct dementia: a cause of mental deterioration in the elderly. Lancet 2: 207-209
10. HAN Y. Y., CARCILLO J. A., RUPPELL R. A., ADELSON P. D., WISNIEWSKI S. R., BELL M. I., JANESKO K. L., MARION D. W., KOCHANEK P. M. (2002). Cerebrospinal fluid Procalcitonin and severe traumatic brain injury in children. Pediatric Critical Care Medicine 3: 39-44
11. HOLMES C., CAIRNS N., LANTOS P., MANN A. (1999). Validity of current clinical criteria for Alzheimer's disease, vascular dementia and dementia with lewy bodies. British Journal of Psychiatry 174: 45-50
12. JEREB M., MULOVIC I., HOJKER S., STRLE F. (2001). Predictive value of serum and cerebrospinal fluid Procalcitonin levels for the diagnosis of bacterial meningitis. Infection 29: 209-212
13. KATSUSE O., ISEKI E., KOSAKA K. (2003). Immunohistochemical study of the expression of cytokines and nitric oxide synthases in brains of patients with dementia with lewy bodies. Neuropathology 23:9-15
14. LOTRIC-FURLAN S., MARASPIN-CARMAN V., CIMPERMAN J., ORINE K., STOPAR T., STRLE F. (2002). Procalcitonin levels in patients with Lyme borreliosis. Wiener Klinische Wochenschrift 114: 530-532
15. MACKENZIE I. R. (2000). Activated microglia in dementia with lewy bodies. Neurology 55: 132-134
16. MACKENZIE I. R. (2001). Cortical Inflammation in Dementia With Lewy Bodies, Arch. Neurol. 58: 519-520
17. MCKEITH 1. G., GALASKO D., KOSAKA K., PERRY E. K., DICKSON D. W., HANSEN L. A., SALMON D. P., LOWE J., MIRRA S. S., BYRNE E. J., LENNOX G., QUINN N. P., EDWARDSON J. A., INCE P. G., BERGERON C., BURNS A., MILLER B. L., LOVESTONE S., COLLERTON D., JANSEN E. N., BALLARD C., DE VOS R. A., WILCOCK G. K., JELLINGER K. A., PERRY R. H. (1996). Consensus guidelines for the clinical and pathologic diagnosis of dementia with lewy bodies (DLB): report of the consortium on DLB international workshop. Neurology 47: 1113-1124
18. MCKEITH I. G., O'BRIEN J. T., BALLARD C. (1999). Diagnosing dementia with lewy bodies. Lancet 354: 1227-1228
19. MCKEITH I. G. (2002). Dementia with lewy bodies. British Journal of Psychiatry 180: 144-147
20. MORGENTHALER N. G., STRUCK J., FISCHER-SCHULZ C., BERGMANN A. (2002). Sensitive immunoluminometric assay for the detection of procalcitonin. Clinical Chemistry 48: 788-789
21. MUELLER B., BECKER K. L., SCHACHINGER H., RICKENBACHER P. R., HUBER P. R., ZIMMERLI W., RITZ R. (2000). Calcitonin precursors are reliable markers of sepsis in a medical intensive care unit. Critical Care Medicine 28: 977-983
22. O'CONNOR E., VENKATESH B., LIPMAN J., MASHONGONYIKA C., HALL J. (2001). Procalcitonin in critical Illness. Critical Care and Resuscitation 3: 236-243
23. RIZZU P., VAN SWIETEN J. C., JOOSSE M., HASEGAWA M., STEVENS M., TIBBEN A., NIERMEIJER M. F., HILLEBRAND M., RAVID R., OOSTRA B. A., GOEDERT M., VAN DUUN C. M., HEUTINK P. (1999). High prevalence of mutations in the microtubule-associated protein tau in a population study of frontotemporal dementia in the Netherlands. American Journal of Human Genetics 64: 414-421
24. SELKOE D. J. (2001). Alzheimer's disease: genes, proteins, and therapy. Physiological Reviews 81: 741-766
25. SHIMETANI N., SHIMETANI K., MORI M. (2001). Levels of three inflammation markers, C-reactive protein, serum amyloid A protein and procalcitonin, in the serum and cerebrospinal fluid of patients with meningitis. Scandinavian Journal of Clinical and Laboratory Investigation 61: 567-574

26. SJOGREN M., FOLKESSON S., BLENNOW K., TARKOWSKI E. (2004). Increased intrathecal inflammatory activity in frontotemporal dementia: pathophysiological implications. Journal of Neurology and Neurosurgical Psychiatry 75: 1107-1111
27. SNIDER R. H. JR., NYLEN E. S., BECKER K. L. (1997). Procalcitonin and its component peptides in systemic inflammation: immunochemical characterization. Journal of Investigative Medicine 45: 552-560
28. TARKOWSKI E. (2002). Cytokines in dementias. Current Drug Targets—Inflammation and Allergy 1: 193-200
29. TARKOWSKI E., LILJEROTH A. M., MINTHON L., TARKOWSKI A., WALLIN A., BLENNOW K. (2003). Cerebral pattern of pro- and anti-inflammatory cytokines in dementias. Brain Research Bulletin 61: 255-260
30. C. E. TEUNISSEN, J. DE VENTE, H. W. M. STEINBUSCH, C. DE BRUIJN (2002), Biochemical markers related to Alzheimer's dementia in serum and cerebrosoinal fluid. Neurobiology of Aging 23, 485-508
31. VARMA A. R., SNOWDEN J. S., LLOYD J. J., TALBOT P. R., MANN D. M., NEARY D. (1999). Evaluation of the NINCDS—ADRDA criteria in the differentiation of Alzheimer's disease and frontotemporal dementia. Journal of Neurology, Neurosurgery and Psychiatry 66: 184-188
32. WHANG K. T., STEINWALD P. M., WHITE J. C., NYLEN E. S., SNIDER R. H., SIMON G. L., GOLDBERG R. L., BECKER K. L. (1998). Serum calcitonin precursors in sepsis and systemic inflammation. Journal of Clinical Endocrinolgy and Metabolism 83: 3296-3301
33. WHICHER I., BIENVENU J., MONNERET G. (2001). Procalcitonin as an acute phase marker. Annals of Clinical Biochemistry 38: 483-893
34. ZHUKAREVA V., VOGELSBERG-RAGAGLIA V., VAN DEERLIN V. M., BRUCE J., SHUCK T., GROSSMAN M., CLARK C. M., ARNOLD S. E., MASLIAH E., GALASKO D., TROJANOWSKI J. Q., LEE V. M. (2001). Loss of brain tau defines novel sporadic and familial tauopathies with frontotemporal dementia. Annals of Neurology 49: 165-175
35. SPENCER C A, LOPRESTI J S, PATEL A, GUTTLER R B, EIGEN A, SHEN D, GRAY D, NICOLOFF J T (1990). Applications of a new chemiluminometric thyrotropin assay to subnormal measurement. J Clin Endocrinol Metab. 1990, 70(2):453-60

The invention claimed is:

1. A method for assisting in the detection and diagnosis of dementias selected from the group consisting of Alzheimer's dementia (AD), dementia with Lewy bodies (DLB), frontotemporal dementia (FTD) and various forms of vascular dementia (VAD), said method comprising:
determining the level of procalcitonin (PCT) in a sample of cerebrospinal fluid (CSF) from an adult patient who is suffering from or, based on clinical manifestations, is suspected of having a dementia selected from the group consisting of Alzheimer's dementia (AD), dementia with Lewy bodies (DLB), frontotemporal dementia (FTD) and various forms of vascular dementia (VAD with the aid of a highly sensitive PCT immunoassay having a functional assay sensitivity (FAS) of 10 ng of PCT per liter (10 ng/1 or 10 pg/ml) or better, said immunoassay comprising contacting the sample of CSF from the adult patient with a pair of antibodies, wherein one of the pair of antibodies binds to calcitonin and the other of the pair of antibodies binds to katacalcin, and at least one of the pair of antibodies is an affinity-purified polyclonal antibody, wherein an increased level of procalcitonin in said sample when compared to levels of PCT in CSF from healthy individuals indicates dementia.

2. The method of claim 1, wherein the increased level of procalcitonin in said sample when compared to levels of PCT in CSF from healthy individuals indicates dementia selected from the group consisting of Alzheimer's dementia (AD), dementia with Lewy bodies (DLB), frontotemporal dementia (FTD) and various forms of vascular dementia (VAD).

3. A method for measuring the level of procalcitonin (PCT) in a sample of cerebrospinal fluid (CSF) from an adult patient who is suffering from or is suspected of having a dementia, said method comprising:
 a) performing an immunoassay for PCT on a sample of CSF from an adult patient who is suffering from or, based on clinical manifestations, is suspected of having a dementia selected from the group consisting of Alzheimer's dementia (AD), dementia with Lewy bodies (DLB), frontotemporal dementia (FTD) and various forms of vascular dementia (VAD), wherein said immunoassay has a functional assay sensitivity (FAS) of 10 ng of PCT per liter (10 ng/1 or 10 pg/ml) or better, and said immunoassay comprises contacting the sample of CSF from the adult patient with a pair of antibodies, wherein one of the pair of antibodies binds to calcitonin and the other of the pair of antibodies binds to katacalcin, and at least one of the pair of antibodies is an affinity-purified polyclonal antibody;
 b) determining the level of PCT in said sample, wherein an increased level of PCT in said sample when compared to levels of PCT in CSF from healthy individuals indicates dementia.

4. The method of claim 3, wherein the increased level of procalcitonin in said sample when compared to levels of PCT in CSF from healthy individuals indicates dementia selected from the group consisting of Alzheimer's dementia (AD), dementia with Lewy bodies (DLB), frontotemporal dementia (FTD) and various forms of vascular dementia (VAD).

5. A method of determining the level of procalcitonin (PCT) in a sample of cerebrospinal fluid (CSF) in an adult patient who is suffering from or, based on clinical manifestations, is suspected of having dementia selected from the group consisting of Alzheimer's dementia (AD), dementia with Lewy bodies (DLB), frontotemporal dementia (FTD) and various forms of vascular dementia (VAD) with the aid of a highly sensitive PCT immunoassay having a functional assay sensitivity (FAS) of 10 ng of PCT per liter (10 ng/1 or 10 pg/ml) or better, said immunoassay comprising contacting the sample of CSF from the adult patient with a pair of antibodies, wherein one of the pair of antibodies binds to calcitonin and the other of the pair binds to katacalcin.

* * * * *